(12) United States Patent
Itagaki

(10) Patent No.: US 7,842,839 B2
(45) Date of Patent: Nov. 30, 2010

(54) METHOD FOR PRODUCING OPTICALLY ACTIVE CYCLOALKYLIDENEBISOXAZOLINE COMPOUND AND INTERMEDIATE THEREOF

(75) Inventor: Makoto Itagaki, Katano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1216 days.

(21) Appl. No.: 10/581,519

(22) PCT Filed: Dec. 21, 2004

(86) PCT No.: PCT/JP2004/019667

§ 371 (c)(1),
(2), (4) Date: Jun. 2, 2006

(87) PCT Pub. No.: WO2005/061438

PCT Pub. Date: Jul. 7, 2005

(65) Prior Publication Data

US 2007/0112201 A1    May 17, 2007

(30) Foreign Application Priority Data

Dec. 22, 2003    (JP) .............................. 2003-424580

(51) Int. Cl.
*C07C 233/00*    (2006.01)
(52) U.S. Cl. ..................................... 564/152; 548/237
(58) Field of Classification Search ................ 564/152; 548/237
See application file for complete search history.

(56) References Cited

FOREIGN PATENT DOCUMENTS

| JP | 4-266887 A | 9/1992 |
| JP | 2004-161963 A | 6/2004 |
| JP | 2004-339163 A | 12/2004 |
| JP | 2005-41786 A | 2/2005 |

OTHER PUBLICATIONS

Denmark, S.E. and Stiff, C.M., "Effect of Ligand Structure in the Bisoxazoline Mediated Asymmetric Addition of Methyllithium to Imines", J. Org. Chem., 2000, vol. 65, No. 18, pp. 5875-5878.

*Primary Examiner*—Kamal A Saeed
*Assistant Examiner*—Samantha L Shterengarts
(74) *Attorney, Agent, or Firm*—Sughrue Mion, PLLC

(57) ABSTRACT

It is provided to an optically active cycloalkylidenebisamidoalcohol compound represented by the formula (3):

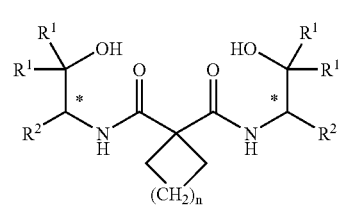

(3)

wherein $R^1$ represents a C1-6 alkyl group, an optionally substituted phenyl group, an optionally substituted aralkyl group or a hydrogen atom, or two $R^1$s, which are bonded to the same carbon atom, are bonded to form a ring together with the carbon atom to which they are bonded, $R^2$ represents a C1-6 alkyl group, an optionally substituted aralkyl group or an optionally substituted phenyl group and * represents an asymmetric center, a method for producing it and a method for producing an optically active cycloalkylidenebisoxazoline compound represented by the formula (4):

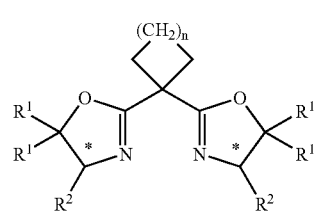

(4)

wherein $R^1$, $R^2$ and * are as defined above, using thereof.

10 Claims, No Drawings

METHOD FOR PRODUCING OPTICALLY ACTIVE CYCLOALKYLIDENEBISOXAZOLINE COMPOUND AND INTERMEDIATE THEREOF

TECHNICAL FIELD

The present invention relates to a method for producing an optically active cycloalkylidenebisoxazoline compound which is an important compound as a ligand of an asymmetric synthesis catalyst.

BACKGROUND ART

An optically active cycloalkylidenebisoxazoline compound has been known as a component of copper bisoxazoline catalyst for asymmetric synthesis of an intermediate of agricultural chemicals and pharmaceuticals such as synthesized pyrethroid type insecticides. As methods for producing the optically active cycloalkylidenebisoxazoline compound, a method for reacting a 2,2-methylenebisoxazoline compound, which is obtained by the reaction of the corresponding optically active aminoalcohol and a malonimidate, with a alkyl dihalide such as 1,2-dibromoethane in the presence of a strong base (e.g. Non-patent document 1). However, it is not always satisfied in the overall yield.

Non-patent document 1: J. Org. Chem., 65, 5875 (2000)

DISCLOSURE OF THE INVENTION

According to the present invention, an optically active cycloalkylidenebisoxazoline compound can be efficiently produced.

That is, one of embodiments of the present invention relates to an optically active cycloalkylidenebisamidoalcohol compound represented by the formula (3):

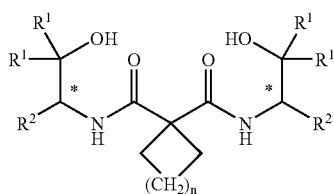

(3)

wherein $R^1$ represents a C1-6 alkyl group, an optionally substituted phenyl group, an optionally substituted aralkyl group or a hydrogen atom, or two $R^1$s, which are bonded to the same carbon atom, are bonded to form a ring together with the carbon atom to which they are bonded, $R^2$ represents a C1-6 alkyl group, an optionally substituted phenyl group or an optionally substituted aralkyl group, n represents an integer of 0 to 3, and * represents an asymmetric center.

Another embodiment relates to a method for producing the above-mentioned optically active cycloalkylidenebisamidoalcohol compound represented by the formula (3), which comprises reacting an optically active aminoalcohol compound represented by the formula (1):

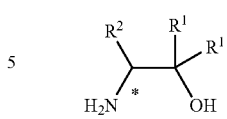

(1)

wherein $R^1$, $R^2$ and * are as defined above, with a cycloalkylidenemalonic acid diester compound represented by the formula (2):

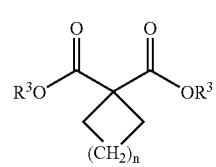

(2)

wherein $R^3$ represents a C1-3 alkyl group and n represents an integer of 0 to 3, in the presence of a lithium compound, and yet another embodiment relates to a method for producing an optically active cycloalkylidenebisoxazoline compound represented by the formula (4):

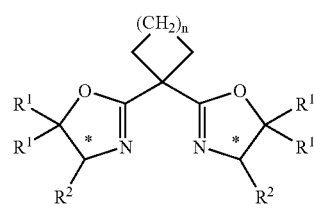

(4)

wherein $R^1$, $R^2$, n and * are as defined in the above formula (3), which comprises reacting the optically active cycloalkylidenebisamidoalcohol compound represented by the formula (3) with a sulfonylation agent in the presence of a basic compound.

BEST MODE FOR CARRYING OUT THE PRESENT INVENTION

The optically active aminoalcohol compound represented by the formula (1) (hereinafter, simply referred to as the optically active aminoalcohol (1)) will be illustrated.

Examples of the C1-6 alkyl group represented by $R^1$ or $R^2$ in the optically active aminoalcohol (1) include a straight or branched chain C1-6 alkyl group such as a methyl, ethyl, n-propyl, isopropyl, n-butyl, isobutyl, tert-butyl, n-pentyl and n-hexyl group.

Examples of the optionally substituted phenyl group represented by $R^1$ or $R^2$ include a phenyl group which may be substituted with at least one selected from a C1-6 alkyl group and a C1-6 alkoxy group such as an unsubstituted phenyl group; a phenyl group substituted with the above-mentioned C1-6 alkyl group such as a 3-methylphenyl and 4-methylphenyl group; and a phenyl group substituted with a C1-6 alkoxy group (e.g. a methoxy, ethoxy, propoxy, butoxy, pentyloxy, and hexyloxy group) such as a 2-methoxyphenyl and 4-methoxyphenyl group.

Examples of the optionally substituted aralkyl group represented by $R^1$ or $R^2$ include an optionally substituted C7-16 aralkyl group (in more detail, for example, a C1-6 alkyl group substituted with a naphthyl group or an optionally substituted phenyl group). As the substituents of the optionally substituted C7-16 aralkyl group, at least one substituent selected from a C1-6 alkyl group and a C1-6 alkoxy group is exemplified. Specific examples of the optionally substituted aralkyl group include a C1-6 alkyl group substituted with a phenyl group which may be substituted with a C1-6 alkyl group or a C1-6 alkoxy group, and a C1-6 alkyl group substituted with a naphthyl group such as a benzyl, 4-methylbenzyl, 4-methoxybenzyl, 1-naphthylmethyl and 2-naphthylmethyl group.

As the ring formed by bonding two $R^1$s, which are bonded to the same carbon atom, together with the carbon atom to which they are bonded, C3-6 cycloalkanes such as a cyclopropane ring, a cyclobutane ring, a cyclopentane ring and a cyclohexane ring are exemplified.

Herein, Examples of the optically active aminoalcohol compound (1) include (R)-2-amino-propanol, (R)-2-amino-1,1-dimethylpropanol, (R)-2-amino-1,1-diethylpropanol, (R)-2-amino-1,1-di(n-propyl)propanol, (R)-2-amino-1,1-diphenylpropanol, (R)-2-amino-1,1-di(4-methylphenyl)propanol, (R)-2-amino-1,1-di(2-methoxyphenyl)propanol, (R)-2-amino-1,1-di(4-methoxyphenyl)propanol, (R)-2-amino-1,1-dibenzylpropanol, 1-((R)-1-aminoethyl)cyclobutanol, 1-((R)-1-aminoethyl)cyclopentanol, 1-((R)-1-aminoethyl)cyclohexanol, (R)-2-amino-3-methylbutanol, (R)-2-amino-3-methyl-1,1-dimethylbutanol, (R) -2-amino-3-methyl-1,1-diethylbutanol, (R)-2-amino-3-methyl-1,1-di(n-propyl)butanol, (R)-2-amino-3-methyl-1,1-diphenylbutanol, (R)-2-amino-3-methyl-1,1-di(4-methylphenyl)butanol, (R)-2-amino-3-methyl-1,1-di(2-methoxyphenyl)butanol, (R)-2-amino-3-methyl-1,1-di(4-methoxyphenyl)butanol, (R)-2-amino-3-methyl-1,1-dibenzylbutanol, 1-((R)-1-amino-2-methylpropyl)cyclobutanol, 1-((R)-1-amino-2-methylpropyl)cyclopentanol, 1-((R)-1-amino-2-methylpropyl)cyclohexanol, (R)-2-amino-4-methylpentanol, (R)-2-amino-4-methyl-1,1-dimethylpentanol, (R)-2-amino-4-methyl-1,1-diethylpentanol, (R)-2-amino-4-methyl-1,1-di(n-propyl)pentanol, (R)-2-amino-4-methyl-1,1-diphenylpentanol, (R)-2-amino-4-methyl-1,1-di(4-methylphenyl)pentanol, (R)-2-amino-4-methyl-1,1-di(2-methoxyphenyl)pentanol, (R)-2-amino-4-methyl-1,1-di(4-methoxyphenyl)pentanol, (R)-2-amino-4-methyl-1,1-dibenzylpentanol, 1-((R)-1-amino-3-methylbutyl)cyclobutanol, 1-((R)-1-amino-3-methylbutyl)cyclopentanol, 1-((R)-1-amino-3-methylbutyl)cyclohexanol, (R)-2-amino-3,3-dimethylbutanol, (R)-2-amino-3,3-dimethyl-1,1-dimethylbutanol, (R)-2-amino-3,3-dimethyl-1,1-diethylbutanol, (R)-2-amino-3,3-dimethyl-1,1-di(n-propyl)butanol, (R)-2-amino-3,3-dimethyl-1,1-diphenylbutanol, (R)-2-amino-3,3-dimethyl-1,1-di(4-methylphenyl)butanol, (R)-2-amino-3,3-dimethyl-1,1-di(2-methoxyphenyl)butanol, (R)-2-amino-3,3-dimethyl-1,1-di(4-methoxyphenyl)butanol, (R)-2-amino-3,3-dimethyl-1,1-dibenzylbutanol, 1-((R)-1-amino-2,2-dimethylpropyl)cyclobutanol, 1-((R)-1-amino-2,2-dimethylpropyl)cyclopentanol, 1-((R)-1-amino-2,2-dimethylpropyl)cyclohexanol, (R)-2-amino-2-phenylethanol, (R)-2-amino-2-phenyl-1,1-dimethylethanol, (R)-2-amino-2-phenyl-1,1-diethylethanol, (R)-2-amino-2-phenyl-1,1-di(n-propyl)ethanol, (R)-2-amino-2-phenyl-1,1-diphenylethanol, (R)-2-amino-2-phenyl-1,1-di(4-methylphenyl)ethanol, (R)-2-amino-2-phenyl-1,1-di(2-methoxyphenyl)ethanol, (R)-2-amino-2-phenyl-1,1-di(4-methoxyphenyl)ethanol, (R)-2-amino-2-phenyl-1,1-dibenzylethanol, 1-((R)-1-amino-1-phenylmethyl)cyclobutanol, 1-((R)-1-amino-1-phenylmethyl)cyclopentanol, 1-((R)-1-amino-1-phenylmethyl)cyclohexanol, (R)-2-amino-3-phenylpropanol, (R)-2-amino-3-phenyl-1,1-dimethylpropanol, (R)-2-amino-3-phenyl-1,1-diethylpropanol, (R)-2-amino-3-phenyl-1,1-di(n-propyl)propanol, (R)-2-amino-3-phenyl-1,1-diphenylpropanol, (R)-2-amino-3-phenyl-1,1-di(4-methylphenyl)propanol, (R)-2-amino-3-phenyl-1,1-di(2-methoxyphenyl)propanol, (R)-2-amino-3-phenyl-1,1-di(4-methoxyphenyl)propanol, (R)-2-amino-3-phenyl-1,1-dibenzylpropanol, 1-((R)-1-amino-2-phenylethyl)cyclobutanol, 1-((R)-1-amino-2-phenylethyl)cyclopentanol and 1-((R)-1-amino-2-phenylethyl)cyclohexanol; and these compounds of which (R) corresponds to (S), and salts thereof such as salts of hydrochloride, salts of sulfuric acid and salts of acetic acid.

The method for producing the above-mentioned optically active aminoalcohol (1) is not particularly limited and for example, those obtained by a known method wherein an easily available optically active amino acid type compound or the ester thereof represented by the formula (6) (hereinafter, simply referred to as the optically active amino acid (6)):

wherein $R^2$ and * are as defined above and $R^4$ represents a C1-4 alkyl group or a hydrogen atom, is a starting material, can be used.

Examples of the C1-4 alkyl group represented by $R^4$ include a methyl, ethyl, n-propyl, isopropyl, n-butyl and tert-butyl group. Among the optically active amino acid (6), examples of the optically active amino acid ester include (R)-alanine methyl ester, (R)-valine methyl ester, (R)-leucine methyl ester, (R)-tert-leucine methyl ester, (R)-phenylglycine methyl ester, (R)-(1-naphthyl)glycine methyl ester, (R)-(2-naphthyl)glycine methyl ester, (R)-phenylalanine methyl ester, and these compounds in which the methyl group of the ester moiety is replaced with an ethyl, propyl or n-butyl group; and these compounds of which (R) corresponds to (S). Examples of the amino acid include (R)-alanine, (R)-valine, (R)-leucine, (R)-tert-leucine, (R)-phenylglycine, (R)-(1-naphthyl)glycine, (R)-(2-naphthyl)glycine, (R)-phenylalanine, and these compounds in which (R) corresponds to (S). Further, the optically active amino acid (6) include salts such as a salt of hydrochloride, a salt of sulfuric acid and a salt of acetic acid of the above-mentioned each compounds.

As the method for producing the optically active aminoalcohol (1) wherein the optically active amino acid (6) is the starting material, when $R^1$ in the formula (1) is the hydrogen atom, the reaction of the optically active amino acid (6) and a borohydride compound is exemplified (e.g. Tetrahedron Letters, 33, 5517(1992), J. Org. Chem., 58, 3568(1993) and Angew. Chem. Int. Ed. Engl., 28, 218(1989)).

Herein, examples of the borohydride compound include boron hydride and a complex of it and a compound which can be coordinated to it such as diborane and borane-tetrahydrofuran complex; a mixture comprising a metal borohydride and an acid; a mixture comprising a metal borohydride and a diester of sulfuric acid; and a metal borohydride. When the ester of the optically active amino acid ($R^4$ is a alkyl group having 1 to 4 carbon atoms) is used as the optically active amino acid (6), only the metal borohydride is preferably used as the borohydride compound. When the optically active amino acid ($R^4$ is a hydrogen atom) is used as the optically active amino acid (5), at least one borohydride compound selected from boron hydride and the complex of it and the compound which can be coordinated to it; the mixture comprising the metal borohydride and the acid; the mixture comprising the metal borohydride and the sulfuric acid diester; and the metal borohydride is preferably used as the borohydride compound.

Examples of the metal borohydride include lithium borohydride, sodium borohydride, potassium borohydride and zinc borohydride, and sodium borohydride is preferably used in terms of availability. Examples of the acid mixed with the metal borohydride include an inorganic acid such as sulfuric acid and hydrochloric acid; and a Lewis acid such as boron trifluoride, zinc chloride, aluminum chloride, titanium tetrachloride, trimethylsilyl chloride and iodine. Examples of the diester of sulfuric acid include dimethyl sulfate and diethyl sulfate.

As the method for producing the optically active aminoalcohol (1) wherein $R^1$ in the formula (1) is the C1-6 alkyl group, the optionally substituted aralkyl group or the optionally substituted phenyl group, for example, a reaction of the optically active amino acid (6) wherein $R^4$ in the formula (6) is the C1-4 alkyl group and a Grignard reagent is exemplified. Examples of the Grignard reagent include a Grignard reagent represented by the formula (7) (hereinafter, simply referred to as the Grignard reagent (7)):

$$R^1MgX \quad (7)$$

wherein $R^1$ is as defined above and X represents a halogen atom, and examples of the halogen atom represented by X include a chlorine atom, a bromine atom and an iodine atom.

Examples of the Grignard reagent (7) include methylmagnesium chloride, ethylmagnesium chloride, n-propylmagnesium chloride, isopropylmagnesium chloride, n-butylmagnesium chloride, isobutylmagnesium chloride, tert-butylmagnesium chloride, n-pentylmagnesium chloride, n-hexylmagnesium chloride, phenylmagnesium chloride, 3-methylphenylmagnesium chloride, 4-methylphenylmagnesium chloride, 2-methoxyphenylmagnesium chloride, 4-methoxyphenylmagnesium chloride, benzylmagnesium chloride, 4-methylbenzylmagnesium chloride, 4-methoxybenzylmagnesium chloride, 1-naphthylmethylmagnesium chloride, 2-naphthylmethylmagnesium chloride, and these compounds in which "chloride" is replaced with "bromide" or "iodide". When $R^1$ represents C1-6 alkyl group and the compound in which two $R^1$s, which are bonded to the same carbon atom, are bonded to form a ring together with the carbon atom to which they are bonded is desired, the Grignard reagent such as butane-1,4-dimagnesium dichloride, pentane-1,5-dimagnesium dichloride, hexane-1,6-dimagnesium dichloride and these compounds in which "chloride" is replaced with "bromide" or "iodide" may be used as the Grignard reagent.

The configuration of the asymmetric center represented by * in the optically active aminoalcohol (1) obtained is the same as that of the optically active amino acid (6) used.

When n is 0 in the cycloalkylidenemalonic acid diester compound represented by the formula (2) (hereinafter, simply referred to as the cycloalkylidenemalonic acid diester (2)), the cycloalkylidenemalonic acid diester (2) represents the cyclopropylidenemalonic acid diester.

Examples of the cycloalkylidenemalonic acid diester (2) include dimethyl cyclopropane-1,1-dicarboxylate, diethyl cyclopropane-1,1-dicarboxylate, dimethyl cyclobutane-1,1-dicarboxylate, diethyl cyclobutane-1,1-dicarboxylate, dimethyl cyclopentane-1,1-dicarboxylate, diethyl cyclopentane-1,1-dicarboxylate, dimethyl cyclohexane-1,1-dicarboxylate and diethyl cyclohexane-1,1-dicarboxylate. As the cycloalkylidenemalonic acid diester (2) having a cyclopropane ring, a cyclobutane ring, a cyclopentane ring or a cyclohexane ring, any one of the methyl esters and the ethyl esters illustrated above is commercially available.

A step for obtaining the optically active cycloalkylidenebisamidoalcohol compound represented by the formula (3) (hereinafter, simply referred to as the optically active cycloalkylidenebisamidoalcohol (3)) by reacting the cycloalkylidenemalonic acid diester (2) with the optically active aminoalcohol (1) will be illustrated.

The reaction of the optically active aminoalcohol (1) and the cycloalkylidenemalonic acid diester (2) is usually carried out in the presence of the lithium compound.

The amount of the cycloalkylidenemalonic acid diester (2) to be used is usually about 0.2 to 2 moles, preferably about 0.4 to 1 mole relative to 1 mole of the optically active aminoalcohol compound (1).

Examples of the lithium compound used in the present invention include lithium hydroxide; a lithium alkoxide such as lithium methoxide and lithium ethoxide; and a lithium halide such as lithium chloride. The amount of them to be used is not particularly limited and it may be catalytic amount and it is usually about 0.0005 to 0.5 mole relative to 1 mole of the diester (2).

The reaction is usually carried out in the presence of a solvent. Examples of the solvent to be used include an aromatic hydrocarbon solvent such as toluene and xylene; an aliphatic hydrocarbon solvent such as hexane, heptane and octane; a halogenated hydrocarbon solvent such as chlorobenzene; and an ether solvent such as tetrahydrofuran and dimethoxyethane. These solvents may be used alone or by mixing two or more of them. The amount of the solvent to be used is not particularly limited and it is usually about 2 to 500 parts by weight relative to 1 part by weight of the optically active aminoalcohol compound (1).

The reaction temperature is not particularly limited and it is usually a range of about 20 to 150° C. The reaction is preferably carried out while removing an alcohol produced as a by-product in the reaction represented by the formula (5) (hereinafter, simply referred to as the alcohol (5)):

$$R^3OH \quad (5)$$

wherein $R^3$ is as above, out the reaction system at a temperature which is a boiling point of the alcohol (5) and above.

The present reaction is usually carried out under an atmospheric condition and may be carried out under a pressurized condition. It can be also carried out under a reduced pressure in order to remove the alcohol (5) like the above.

The present reaction is carried out by mixing the lithium compound, the optically active aminoalcohol (1) and the cycloalkylidenemalonic acid diester (2), and if necessary in the presence of the solvent, and the mixing order is not particularly limited. For example, it may be carried out by adjusting a reaction temperature after mixing them at a time and by adding the cycloalkylidenemalonic acid diester (2) to a mixture of the lithium compound and the optically active aminoalcohol (1) which is adjusted to the reaction temperature.

After completion of the reaction, for example, the optically active cycloalkylidenebisamidoalcohol (3) can be obtained by adding water to the reaction mixture, if necessary conducting extracting treatment using a water-insoluble organic solvent such as toluene and ethyl acetate, and concentrating the organic layer obtained. When the product is precipitated from the reaction mixture, the product can be isolated by the operation such as filtration. The optically active cycloalkylidenebisamidoalcohol (3) obtained can be further purified by a conventional method such as distillation and recrystallization.

The configuration of the asymmetric center represented by * in the optically active cycloalkylidenebisamidoalcohol (3) thus obtained is the same as that of the optically active aminoalcohol (1) used.

Examples of the optically active cycloalkylidenebisamidoalcohol (3) include N,N'-bis[(R)-1-methyl-2-hydroxyethyl]cyclopropane-1,1-dicarboxamide, N,N'-bis[(R)-1,2-dimethyl-2-hydroxypropyl]cyclopropane-1,1-dicarboxamide, N,N'-bis[(R)-1-methyl-2-ethyl-2-hydroxybutyl]cyclopropane-1,1-dicarboxamide, N,N'-bis[(R)-1-methyl-2-n-propyl-2-hydroxypentyl]cyclopropane-1,1-dicarboxamide, N,N'-bis[(R)-1-methyl-2,2-diphenyl-2-hydroxyethyl]cyclopropane-1,1-dicarboxamide, N,N'-bis[(R)-1-methyl-2,2-di(4-methylphenyl)-2-hydroxyethyl]cyclopropane-1,1-dicarboxamide, N,N'-bis[(R)-1-methyl-2,2-di(2-methoxyphenyl)-2-hydroxyethyl]cyclopropane-1,1-dicarboxamide, N,N'-bis[(R)-1-methyl-2,2-di(4-methoxyphenyl)-2-hydroxyethyl]cyclopropane-1,1-dicarboxamide, N,N'-bis[(R)-1-methyl-2-benzyl-2-hydroxy-3-phenylpropyl]cyclopropane-1,1-dicarboxamide, N,N'-bis[(R)-1-(1-hydroxycyclobutyl)ethyl]cyclopropane-1,1-dicarboxamide, N,N'-bis[(R)-1-(1-hydroxycyclopentyl)ethyl]cyclopropane-1,1-dicarboxamide, N,N'-bis[(R)-1-(1-hydroxycyclohexyl)ethyl]cyclopropane-1,1-dicarboxamide, N,N'-bis[(R)-1-isopropyl-2-hydroxyethyl]cyclopropane-1,1-dicarboxamide, N,N'-bis[(R)-1-isopropyl-2-methyl-2-hydroxypropyl]cyclopropane-1,1-dicarboxamide, N,N'-bis[(R)-1-isopropyl-2-ethyl-2-hydroxybutyl]cyclopropane-1,1-dicarboxamide, N,N'-bis[(R)-1-isopropyl-2-n-propyl-2-hydroxypentyl]cyclopropane-1,1-dicarboxamide, N,N'-bis[(R)-1-isopropyl-2,2-diphenyl-2-hydroxyethyl]cyclopropane-1,1-dicarboxamide, N,N'-bis[(R)-1-isopropyl-2,2-di(4-methylphenyl)-2-hydroxyethyl]cyclopropane-1,1-dicarboxamide, N,N'-bis[(R)-1-isopropyl-2,2-di(2-methoxyphenyl)-2-hydroxyethyl]cyclopropane-1,1-dicarboxamide, N,N'-bis[(R)-1-isopropyl-2,2-di(4-methoxyphenyl)-2-hydroxyethyl]cyclopropane-1,1-dicarboxamide, N,N'-bis[(R)-1-isopropyl-2-benzyl-2-hydroxy-3-phenylpropyl]cyclopropane-1,1-dicarboxamide, N,N'-bis[(R)-2-methyl-1-(1-hydroxycyclobutyl)propyl]cyclopropane-1,1-dicarboxamide, N,N'-bis[(R)-2-methyl-1-(1-hydroxycyclopentyl)propyl]cyclopropane-1,1-dicarboxamide, N,N'-bis[(R)-2-methyl-1-(1-hydroxycyclohexyl)propyl]cyclopropane-1,1-dicarboxamide, N,N'-bis[(R)-1-isobutyl-2-hydroxyethyl]cyclopropane-1,1-dicarboxamide, N,N'-bis[(R)-1-isobutyl-2-methyl-2-hydroxypropyl]cyclopropane-1,1-dicarboxamide, N,N'-bis[(R)-1-isobutyl-2-ethyl-2-hydroxybutyl]cyclopropane-1,1-dicarboxamide, N,N'-bis[(R)-1-isobutyl-2-n-propyl-2-hydroxypentyl]cyclopropane-1,1-dicarboxamide, N,N'-bis[(R)-1-isobutyl-2,2-diphenyl-2-hydroxyethyl]cyclopropane-1,1-dicarboxamide, N,N'-bis[(R)-1-isobutyl-2,2-di(4-methylphenyl)-2-hydroxyethyl]cyclopropane-1,1-dicarboxamide, N,N'-bis[(R)-1-isobutyl-2,2-di(2-methoxyphenyl)-2-hydroxyethyl]cyclopropane-1,1-dicarboxamide, N,N'-bis[(R)-1-isobutyl-2,2-di(4-methoxyphenyl)-2-hydroxyethyl]cyclopropane-1,1-dicarboxamide, N,N'-bis[(R)-1-isobutyl-2-benzyl-2-hydroxy-3-phenylpropyl]cyclopropane-1,1-dicarboxamide, N,N'-bis[(R)-3-methyl-1-(1-hydroxycyclobutyl)butyl]cyclopropane-1,1-dicarboxamide, N,N'-bis[(R)-3-methyl-1-(1-hydroxycyclopentyl)butyl]cyclopropane-1,1-dicarboxamide, N,N'-bis[(R)-3-methyl-1-(1-hydroxycyclohexyl)butyl]cyclopropane-1,1-dicarboxamide, N,N'-bis[(R)-1-tert-butyl-2-hydroxyethyl]cyclopropane-1,1-dicarboxamide, N,N'-bis[(R)-1-tert-butyl-2-methyl-2-hydroxypropyl]cyclopropane-1,1-dicarboxamide, N,N'-bis[(R)-1-tert-butyl-2-ethyl-2-hydroxybutyl]cyclopropane-1,1-dicarboxamide, N,N'-bis[(R)-1-tert-butyl-2-n-propyl-2-hydroxypentyl]cyclopropane-1,1-dicarboxamide, N,N'-bis[(R)-1-tert-butyl-2,2-diphenyl-2-hydroxyethyl]cyclopropane-1,1-dicarboxamide, N,N'-bis[(R)-1-tert-butyl-2,2-di(4-methylphenyl)-2-hydroxyethyl]cyclopropane-1,1-dicarboxamide, N,N'-bis[(R)-1-tert-butyl-2,2-di(2-methoxyphenyl)-2-hydroxyethyl]cyclopropane-1,1-dicarboxamide, N,N'-bis[(R)-1-tert-butyl-2,2-di(4-methoxyphenyl)-2-hydroxyethyl]cyclopropane-1,1-dicarboxamide, N,N'-bis[(R)-1-tert-butyl-2-benzyl-2-hydroxy-3-phenylpropyl]cyclopropane-1,1-dicarboxamide, N,N'-bis[(R)-2,2-dimethyl-1-(1-hydroxycyclobutyl)propyl]cyclopropane-1,1-dicarboxamide, N,N'-bis[(R)-2,2-dimethyl-1-(1-hydroxycyclopentyl)propyl]cyclopropane-1,1-dicarboxamide, N,N'-bis[(R)-2,2-dimethyl-1-(1-hydroxycyclohexyl)propyl]cyclopropane-1,1-dicarboxamide, N,N'-bis[(R)-1-phenyl-2-hydroxyethyl]cyclopropane-1,1-dicarboxamide, N,N'-bis[(R)-1-phenyl-2-methyl-2-hydroxypropyl]cyclopropane-1,1-dicarboxamide, N,N'-bis[(R)-1-phenyl-2-ethyl-2-hydroxybutyl]cyclopropane-1,1-dicarboxamide, N,N'-bis[(R)-1-phenyl-2-n-propyl-2-hydroxypentyl]cyclopropane-1,1-dicarboxamide, N,N'-bis[(R)-1-phenyl-2,2-diphenyl-2-hydroxyethyl]cyclopropane-1,1-dicarboxamide, N,N'-bis[(R)-1-phenyl-2,2-di(4-methylphenyl)-2-hydroxyethyl]cyclopropane-1,1-dicarboxamide, N,N'-bis[(R)-1-phenyl-2,2-di(2-methoxyphenyl)-2-hydroxyethyl]cyclopropane-1,1-dicarboxamide, N,N'-bis[(R)-1-phenyl-2,2-di(4-methoxyphenyl)-2-hydroxyethyl]cyclopropane-1,1-dicarboxamide, N,N'-bis[(R)-1-phenyl-2-benzyl-2-hydroxy-3-phenylpropyl]cyclopropane-1,1-dicarboxamide, N,N'-bis[(R)-1-phenyl-1-(1-hydroxycyclobutyl)methyl]cyclopropane-1,1-dicarboxamide, N,N'-bis[R]-1-phenyl-1-(1-hydroxycyclopentyl)methyl]cyclopropane-1,1-dicarboxamide, N,N'-bis[(R)-1-phenyl-1-(1-hydroxycyclohexyl)methyl]cyclopropane-1,1-dicarboxamide, N,N'-bis[(R)-1-benzyl-2-hydroxyethyl]cyclopropane-1,1-dicarboxamide, N,N'-bis[(R)-1-benzyl-2-methyl-2-hydroxypropyl]cyclopropane-1,1-dicarboxamide, N,N'-bis[(R)-1-benzyl-2-ethyl-2-hydroxybutyl]cyclopropane-1,1-dicarboxamide, N,N'-bis[(R)-1-benzyl-2-n-propyl-2-hydroxypentyl]cyclopropane-1,1-dicarboxamide, N,N'-bis[(R)-1-benzyl-2,2-diphenyl-2-hydroxyethyl]cyclopropane-1,1-dicarboxamide, N,N'-bis[(R)-1-benzyl-2,2-di(4-methylphenyl)-2-hydroxyethyl]cyclopropane-1,1-dicarboxamide, N,N'-bis[(R)-1-benzyl-2,2-di(2-methoxyphenyl)-2-hydroxyethyl]cyclopropane-1,1-dicarboxamide, N,N'-bis[(R)-1-benzyl-2,2-di(4-methoxyphenyl)-2-hydroxyethyl]cyclopropane-1,1-dicarboxamide, N,N'-bis[(R)-1-benzyl-2-benzyl-2-hydroxy-3-phenylpropyl]cyclopropane-1,1-dicarboxamide, N,N'-bis[(R)-2-phenyl-1-(1-hydroxycyclobutyl)ethyl]cyclopropane-1,1-dicarboxamide, N,N'-bis[(R)-2-phenyl-1-(1-hydroxycyclopentyl)ethyl]cyclopropane-1,1-dicarboxamide, N,N'-bis[(R)-2-phenyl-1-(1-hydroxycyclohexyl)ethyl]cyclopropane-1,1-dicarboxamide, N,N'-bis[(R)-1-methyl-2-hydroxyethyl]cyclobutane-1,1-dicarboxamide, N,N'-bis[(R)-1,2-dimethyl-2-hydroxypropyl]cyclobutane-1,1-dicarboxamide, N,N'-bis[(R)-1-methyl- 2-ethyl-2-hydroxybutyl]cyclobutane-1,1-dicarboxamide, N,N'-bis[(R)-1-methyl-2-n-propyl-2-hydroxypentyl]cyclobutane-1,1-dicarboxamide, N,N'-bis[(R)-1-methyl-2,2-diphenyl-2-hydroxyethyl]cyclobutane-1,1-dicarboxamide, N,N'-bis[(R)-1-methyl-2,2-di(4-methylphenyl)-2-hydroxyethyl]cyclobutane-1,1-dicarboxamide, N,N'-bis[(R)-1-methyl-2,2-di(2-methoxyphenyl)-2-hydroxyethyl]cyclobutane-1,1-dicarboxamide, N,N'-bis[(R)-1-methyl-2,2-di(4-methoxyphenyl)-2-hydroxyethyl]cyclobutane-1,1-dicarboxamide, N,N'-bis[(R)-1-methyl-2-benzyl-2-hydroxy-3-phenylpropyl]cyclobutane-1,1-dicarboxamide, N,N'-bis[(R)-1-(1-hydroxycyclobutyl)ethyl]cyclobutane-1,1-dicarboxamide, N,N'-bis[(R)-1-(1-hydroxycyclopentyl)ethyl]cyclobutane-1,1-dicarboxamide, N,N'-bis[(R)-1-(1-hydroxycyclohexyl)ethyl]cyclobutane-1,1-dicarboxamide, N,N'-bis[(R)-1-isopropyl-2-hydroxyethyl]cyclobutane-1,1-dicarboxamide, N,N'-bis[(R)-1-isopropyl-2-methyl-2-hydroxypropyl]cyclobutane-1,1-dicarboxamide, N,N'-bis[(R)-1-isopropyl-2-ethyl-2-hydroxybutyl]cyclobutane-1,1-dicarboxamide, N,N'-bis[(R)-1-isopropyl-2-n-propyl-2-hydroxypentyl]cyclobutane-1,1-dicarboxamide, N,N'-bis[(R)-1-isopropyl-2,2-diphenyl-2-hydroxyethyl]cyclobutane-1,1-dicarboxamide, N,N'-bis[(R)-1-isopropyl-2,2-di(4-methylphenyl)-2-hydroxyethyl]cyclobutane-1,1-dicarboxamide, N,N'-bis[(R)-1-isopropyl-2,2-di(2-methoxyphenyl)-2-hydroxyethyl]cyclobutane-1,1-dicarboxamide, N,N'-bis[(R)-1-isopropyl-2,2-di(4-methoxyphenyl)-2-hydroxyethyl]cyclobutane-1,1-dicarboxamide, N,N'-bis[(R)-1-isopropyl-2-benzyl-2-hydroxy-3-phenylpropyl]cyclobutane-1,1-dicarboxamide, N,N'-bis[(R)-2-methyl-1-(1-hydroxycyclobutyl)propyl]cyclobutane-1,1-dicarboxamide, N,N'-bis[(R)-2-methyl-1-(1-hydroxycyclopentyl)propyl]cyclobutane-1,1-dicarboxamide, N,N'-bis[(R)-2-methyl-1-(1-hydroxycyclohexyl)propyl]cyclobutane-1,1-dicarboxamide, N,N'-bis[(R)-1-isobutyl-2-hydroxyethyl]cyclobutane-1,1-dicarboxamide, N,N'-bis[(R)-1-isobutyl-2-methyl-2-hydroxypropyl]cyclobutane-1,1-dicarboxamide, N,N'-bis[(R)-1-isobutyl-2-ethyl-2-hydroxybutyl]cyclobutane-1,1-dicarboxamide, N,N'-bis[(R)-1-isobutyl-2-n-propyl-2-hydroxypentyl]cyclobutane-1,1-dicarboxamide, N,N'-bis[(R)-1-isobutyl-2,2-diphenyl-2-hydroxyethyl]cyclobutane-1,1-dicarboxamide, N,N'-bis[(R)-1-isobutyl-2,2-di(4-methylphenyl)-2-hydroxyethyl]cyclobutane-1,1-dicarboxamide, N,N'-bis[(R)-1-isobutyl-2,2-di(2-methoxyphenyl)-2-hydroxyethyl]cyclobutane-1,1-dicarboxamide, N,N'-bis[(R)-1-isobutyl-2,2-di(4-methoxyphenyl)-2-hydroxyethyl]cyclobutane-1,1-dicarboxamide, N,N'-bis[(R)-1-isobutyl-2-benzyl-2-hydroxy-3-phenylpropyl]cyclobutane-1,1-dicarboxamide, N,N'-bis[(R)-3-methyl-1-(1-hydroxycyclobutyl)butyl]cyclobutane-1,1-dicarboxamide, N,N'-bis[(R)-3-methyl-1-(1-hydroxycyclopentyl)butyl]cyclobutane-1,1-dicarboxamide, N,N'-bis[(R)-3-methyl-1-(1-hydroxycyclohexyl)butyl]cyclobutane-1,1-dicarboxamide, N,N'-bis[(R)-1-tert-butyl-2-hydroxyethyl]cyclobutane-1,1-dicarboxamide, N,N'-bis[(R)-1-tert-butyl-2-methyl-2-hydroxypropyl]cyclobutane-1,1-dicarboxamide, N,N'-bis[(R)-1-tert-butyl-2-ethyl-2-hydroxybutyl]cyclobutane-1,1-dicarboxamide, N,N'-bis[(R)-1-tert-butyl-2-n-propyl-2-hydroxypentyl]cyclobutane-1,1-dicarboxamide, N,N'-bis[(R)-1-tert-butyl-2,2-diphenyl-2-hydroxyethyl]cyclobutane-1,1-dicarboxamide, N,N'-bis[(R)-1-tert-butyl-2,2-di(4-methylphenyl)-2-hydroxyethyl]cyclobutane-1,1-dicarboxamide, N,N'-bis[(R)-1-tert-butyl-2,2-di(2-methoxyphenyl)-2-hydroxyethyl]cyclobutane-1,1-dicarboxamide, N,N'-bis[(R)-1-tert-butyl-2,2-di(4-methoxyphenyl)-2-hydroxyethyl]cyclobutane-1,1-dicarboxamide, N,N'-bis[(R)-1-tert-butyl-2-benzyl-2-hydroxy-3-phenylpropyl]cyclobutane-1,1-dicarboxamide, N,N'-bis[(R)-2,2-dimethyl-1-(1-hydroxycyclobutyl)propyl]cyclobutane-1,1-dicarboxamide, N,N'-bis[(R)-2,2-dimethyl-1-(1-hydroxycyclopentyl)propyl]cyclobutane-1,1-dicarboxamide, N,N'-bis[(R)-2,2-dimethyl-1-(1-hydroxycyclohexyl)propyl]cyclobutane-1,1-dicarboxamide, N,N'-bis[(R)-1-phenyl-2-hydroxyethyl]cyclobutane-1,1-dicarboxamide, N,N'-bis[(R)-1-phenyl-2-methyl-2-hydroxypropyl]cyclobutane-1,1-dicarboxamide, N,N'-bis[(R)-1-phenyl-2-ethyl-2-hydroxybutyl]cyclobutane-1,1-dicarboxamide, N,N'-bis[(R)-1-phenyl-2-n-propyl-2-hydroxypentyl]cyclobutane-1,1-dicarboxamide, N,N'-bis[(R)-1-phenyl-2,2-diphenyl-2-hydroxyethyl]cyclobutane-1,1-dicarboxamide, N,N'-bis[(R)-1-phenyl-2,2-di(4-methylphenyl)-2-hydroxyethyl]cyclobutane-1,1-dicarboxamide, N,N'-bis[(R)-1-phenyl-2,2-di(2-methoxyphenyl)-2-hydroxyethyl]cyclobutane-1,1-dicarboxamide, N,N'-bis[(R)-1-phenyl-2,2-di(4-methoxyphenyl)-2-hydroxyethyl]cyclobutane-1,1-dicarboxamide, N,N'-bis[(R)-1-phenyl-2-benzyl-2-hydroxy-3-phenylpropyl]cyclobutane-1,1-dicarboxamide, N,N'-bis[(R)-1-phenyl-1-(1-hydroxycyclobutyl)methyl]cyclobutane-1,1-dicarboxamide, N,N'-bis[R]-1-phenyl-1-(1-hydroxycyclopentyl)methyl]cyclobutane-1,1-dicarboxamide, N,N'-bis((R)-1-phenyl-1-(1-hydroxycyclohexyl)methyl]cyclobutane-1,1-dicarboxamide, N,N'-bis[(R)-1-benzyl-2-hydroxyethyl]cyclobutane-1,1-dicarboxamide, N,N'-bis[(R)-1-benzyl-2-methyl-2-hydroxypropyl]cyclobutane-1,1-dicarboxamide, N,N'-bis[(R)-1-benzyl-2-ethyl-2-hydroxybutyl]cyclobutane-1,1-dicarboxamide, N,N'-bis[(R)-1-benzyl-2-n-propyl-2-hydroxypentyl]cyclobutane-1,1-dicarboxamide, N,N'-bis[(R)-1-benzyl-2,2-diphenyl-2-hydroxyethyl]cyclobutane-1,1-dicarboxamide, N,N'-bis[(R)-1-benzyl-2,2-di(4-methylphenyl)-2-hydroxyethyl]cyclobutane-1,1-dicarboxamide, N,N'-bis[(R)-1-benzyl-2,2-di(2-methoxyphenyl)-2-hydroxyethyl]cyclobutane-1,1-dicarboxamide, N,N'-bis[(R)-1-benzyl-2,2-di(4-methoxyphenyl)-2-hydroxyethyl]cyclobutane-1,1-dicarboxamide, N,N'-bis[(R)-1-benzyl-2-benzyl-2-hydroxy-3-phenylpropyl]cyclobutane-1,1-dicarboxamide, N,N'-bis[(R)-2-phenyl-1-(1-hydroxycyclobutyl)ethyl]cyclobutane-1,1-dicarboxamide, N,N'-bis[(R)-2-phenyl-1-(1-hydroxycyclopentyl)ethyl]cyclobutane-1,1-dicarboxamide, N,N'-bis[(R)-2-phenyl-1-(1-hydroxycyclohexyl)ethyl]cyclobutane-1,1-dicarboxamide, N,N'-bis[(R)-1-methyl-2-hydroxyethyl]cyclopentane-1,1-dicarboxamide, N,N'-bis[(R)-1,2-dimethyl-2-hydroxypropyl]cyclopentane-1,1-dicarboxamide, N,N'-bis[(R)-1-methyl-2-ethyl-2-hydroxybutyl]cyclopentane-1,1-dicarboxamide, N,N'-bis[(R)-1-methyl-2-n-propyl-2-hydroxypentyl]cyclopentane-1,1-dicarboxamide, N,N'-bis[(R)-1-methyl-2,2-diphenyl-2-hydroxyethyl]cyclopentane-1,1-dicarboxamide, N,N'-bis[(R)-1-methyl-2,2-di(4-methylphenyl)-2-hydroxyethyl]cyclopentane-1,1-dicarboxamide, N,N'-bis[(R)-1-methyl-2,2-di(2-methoxyphenyl)-2-hydroxyethyl]cyclopentane-1,1-dicarboxamide, N,N'-bis[(R)-1-methyl-2,2-di(4-methoxyphenyl)-2-hydroxyethyl]cyclopentane-1,1-dicarboxamide, N,N'-bis[(R)-1-methyl-2-benzyl-2-hydroxy-3-phenylpropyl]cyclopentane-1,1-dicarboxamide, N,N'-bis[(R)-1-(1-hydroxycyclobutyl)ethyl]cyclopentane-1,1-dicarboxamide, N,N'-bis[(R)-1-(1-hydroxycyclopentyl)

ethyl]cyclopentane-1,1-dicarboxamide, N,N'-bis[(R)-1-(1-hydroxycyclohexyl)ethyl]cyclopentane-1,1-dicarboxamide,
N,N'-bis[(R)-1-isopropyl-2-hydroxyethyl]cyclopentane-1,1-dicarboxamide, N,N'-bis[(R)-1-isopropyl-2-methyl-2-hydroxypropyl]cyclopentane-1,1-dicarboxamide, N,N'-bis[(R)-1-isopropyl-2-ethyl-2-hydroxybutyl]cyclopentane-1,1-dicarboxamide, N,N'-bis[(R)-1-isopropyl-2-n-propyl-2-hydroxypentyl]cyclopentane-1,1-dicarboxamide, N,N'-bis[(R)-1-isopropyl-2,2-diphenyl-2-hydroxyethyl]cyclopentane-1,1-dicarboxamide, N,N'-bis[(R)-1-isopropyl-2,2-di(4-methylphenyl)-2-hydroxyethyl]cyclopentane-1,1-dicarboxamide, N,N'-bis[(R)-1-isopropyl-2,2-di(2-methoxyphenyl)-2-hydroxyethyl]cyclopentane-1,1-dicarboxamide, N,N'-bis[(R)-1-isopropyl-2,2-di(4-methoxyphenyl)-2-hydroxyethyl]cyclopentane-1,1-dicarboxamide, N,N'-bis[(R)-1-isopropyl-2-benzyl-2-hydroxy-3-phenylpropyl]cyclopentane-1,1-dicarboxamide, N,N'-bis[(R)-2-methyl-1-(1-hydroxycyclobutyl)propyl]cyclopentane-1,1-dicarboxamide, N,N'-bis[(R)-2-methyl-1-(1-hydroxycyclopentyl)propyl]cyclopentane-1,1-dicarboxamide, N,N'-bis[(R)-2-methyl-1-(1-hydroxycyclohexyl)propyl]cyclopentane-1,1-dicarboxamide, N,N'-bis[(R)-1-isobutyl-2-hydroxyethyl]cyclopentane-1,1-dicarboxamide, N,N'-bis[(R)-1-isobutyl-2-methyl-2-hydroxypropyl]cyclopentane-1,1-dicarboxamide, N,N'-bis[(R)-1-isobutyl-2-ethyl-2-hydroxybutyl]cyclopentane-1,1-dicarboxamide, N,N'-bis[(R)-1-isobutyl-2-n-propyl-2-hydroxypentyl]cyclopentane-1,1-dicarboxamide, N,N'-bis[(R)-1-isobutyl-2,2-diphenyl-2-hydroxyethyl]cyclopentane-1,1-dicarboxamide, N,N'-bis[(R)-1-isobutyl-2,2-di(4-methylphenyl)-2-hydroxyethyl]cyclopentane-1,1-dicarboxamide, N,N'-bis[(R)-1-isobutyl-2,2-di(2-methoxyphenyl)-2-hydroxyethylcyclopentane-1,1-dicarboxamide, N,N'-bis[(R)-1-isobutyl-2,2-di(4-methoxyphenyl)-2-hydroxyethyl]cyclopentane-1,1-dicarboxamide, N,N'-bis[(R)-1-isobutyl-2-benzyl-2-hydroxy-3-phenylpropyl]cyclopentane-1,1-dicarboxamide, N,N'-bis[(R)-3-methyl-1-(1-hydroxycyclobutyl)butyl]cyclopentane-1,1-dicarboxamide, N,N'-bis[(R)-3-methyl-1-(1-hydroxycyclopentyl)butyl]cyclopentane-1,1-dicarboxamide, N,N'-bis[(R)-3-methyl-1-(1-hydroxycyclohexyl)butyl]cyclopentane-1,1-dicarboxamide, N,N'-bis[(R)-1-tert-butyl-2-hydroxyethyl]cyclopentane-1,1-dicarboxamide, N,N'-bis[(R)-1-tert-butyl-2-methyl-2-hydroxypropyl]cyclopentane-1,1-dicarboxamide, N,N'-bis[(R)-1-tert-butyl-2-ethyl-2-hydroxybutyl]cyclopentane-1,1-dicarboxamide, N,N'-bis[(R)-1-tert-butyl-2-n-propyl-2-hydroxypentyl]cyclopentane-1,1-dicarboxamide, N,N'-bis[(R)-1-tert-butyl-2,2-diphenyl-2-hydroxyethyl]cyclopentane-1,1-dicarboxamide, N,N'-bis[(R)-1-tert-butyl-2,2-di(4-methylphenyl)-2-hydroxyethyl]cyclopentane-1,1-dicarboxamide, N,N'-bis[(R)-1-tert-butyl-2,2-di(2-methoxyphenyl)-2-hydroxyethyl]cyclopentane-1,1-dicarboxamide, N,N'-bis[(R)-1-tert-butyl-2,2-di(4-methoxyphenyl)-2-hydroxyethyl]cyclopentane-1,1-dicarboxamide, N,N'-bis[(R)-1-tert-butyl-2-benzyl-2-hydroxy-3-phenylpropyl]cyclopentane-1,1-dicarboxamide, N,N'-bis[(R)-2,2-dimethyl-1-(1-hydroxycyclobutyl)propyl]cyclopentane-1,1-dicarboxamide, N,N'-bis[(R)-2,2-dimethyl-1-(1-hydroxycyclopentyl)propyl]cyclopentane-1,1-dicarboxamide, N,N'-bis[(R)-2,2-dimethyl-1-(1-hydroxycyclohexyl)propyl]cyclopentane-1,1-dicarboxamide, N,N'-bis[(R)-1-phenyl-2-hydroxyethyl]cyclopentane-1,1-dicarboxamide, N,N'-bis[(R)-1-phenyl-2-methyl-2-hydroxypropyl]cyclopentane-1,1-dicarboxamide, N,N'-bis[(R)-1-phenyl-2-ethyl-2-hydroxybutyl]cyclopentane-1,1-dicarboxamide, N,N'-bis[(R)-1-phenyl-2-n-propyl-2-hydroxypentyl]cyclopentane-1,1-dicarboxamide, N,N'-bis[(R)-1-phenyl-2,2-diphenyl-2-hydroxyethyl]cyclopentane-1,1-dicarboxamide, N,N'-bis[(R)-1-phenyl-2,2-di(4-methylphenyl)-2-hydroxyethyl]cyclopentane-1,1-dicarboxamide, N,N'-bis[(R)-1-phenyl-2,2-di(2-methoxyphenyl)-2-hydroxyethyl]cyclopentane-1,1-dicarboxamide, N,N'-bis[(R)-1-phenyl-2,2-di(4-methoxyphenyl)-2-hydroxyethyl]cyclopentane-1,1-dicarboxamide, N,N'-bis[(R)-1-phenyl-2-benzyl-2-hydroxy-3-phenylpropyl]cyclopentane-1,1-dicarboxamide, N,N'-bis[(R)-1-phenyl-1-(1-hydroxycyclobutyl)methyl]cyclopentane-1,1-dicarboxamide, N,N'-bis[R]-1-phenyl-1-(1-hydroxycyclopentyl)methyl]cyclopentane-1,1-dicarboxamide, N,N'-bis[(R)-1-phenyl-1-(1-hydroxycyclohexyl)methyl]cyclopentane-1,1-dicarboxamide, N,N'-bis[(R)-1-benzyl-2-hydroxyethyl]cyclopentane-1,1-dicarboxamide, N,N'-bis[(R)-1-benzyl-2-methyl-2-hydroxypropyl]cyclopentane-1,1-dicarboxamide, N,N'-bis[(R)-1-benzyl-2-ethyl-2-hydroxybutyl]cyclopentane-1,1-dicarboxamide, N,N'-bis[(R)-1-benzyl-2-n-propyl-2-hydroxypentyl]cyclopentane-1,1-dicarboxamide, N,N'-bis[(R)-1-benzyl-2,2-diphenyl-2-hydroxyethyl]cyclopentane-1,1-dicarboxamide, N,N'-bis[(R)-1-benzyl-2,2-di(4-methylphenyl)-2-hydroxyethyl]cyclopentane-1,1-dicarboxamide, N,N'-bis[(R)-1-benzyl-2,2-di(2-methoxyphenyl)-2-hydroxyethyl]cyclopentane-1,1-dicarboxamide, N,N'-bis[(R)-1-benzyl-2,2-di(4-methoxyphenyl)-2-hydroxyethyl]cyclopentane-1,1-dicarboxamide, N,N'-bis[(R)-1-benzyl-2-benzyl-2-hydroxy-3-phenylpropyl]cyclopentane-1,1-dicarboxamide, N,N'-bis[(R)-2-phenyl-1-(1-hydroxycyclobutyl)ethyl]cyclopentane-1,1-dicarboxamide, N,N'-bis[(R)-2-phenyl-1-(1-hydroxycyclopentyl)ethyl]cyclopentane-1,1-dicarboxamide, N,N'-bis[(R)-2-phenyl-1-(1-hydroxycyclohexyl)ethyl]cyclopentane-1,1-dicarboxamide, N,N'-bis[(R)-1-methyl-2-hydroxyethyl]cyclohexane-1,1-dicarboxamide, N,N'-bis[(R)-1,2-dimethyl-2-hydroxypropyl]cyclohexane-1,1-dicarboxamide, N,N'-bis[(R)-1-methyl-2-ethyl-2-hydroxybutyl]cyclohexane-1,1-dicarboxamide, N,N'-bis[(R)-1-methyl-2-n-propyl-2-hydroxypentyl]cyclohexane-1,1-dicarboxamide, N,N'-bis[(R)-1-methyl-2,2-diphenyl-2-hydroxyethyl]cyclohexane-1,1-dicarboxamide, N,N'-bis[(R)-1-methyl-2,2-di(4-methylphenyl)-2-hydroxyethyl]cyclohexane-1,1-dicarboxamide, N,N'-bis[(R)-1-methyl-2,2-di(2-methoxyphenyl)-2-hydroxyethyl]cyclohexane-1,1-dicarboxamide, N,N'-bis[(R)-1-methyl-2,2-di(4-methoxyphenyl)-2-hydroxyethyl]cyclohexane-1,1-dicarboxamide, N,N'-bis[(R)-1-methyl-2-benzyl-2-hydroxy-3-phenylpropyl]cyclohexane-1,1-dicarboxamide, N,N'-bis[(R)-1-(1-hydroxycyclobutyl)ethyl]cyclohexane-1,1-dicarboxamide, N,N'-bis[(R)-1-(1-hydroxycyclopentyl)ethyl]cyclohexane-1,1-dicarboxamide, N,N'-bis[(R)-1-(1-hydroxycyclohexyl)ethyl]cyclohexane-1,1-dicarboxamide, N,N'-bis[(R)-1-isopropyl-2-hydroxyethyl]cyclohexane-1,1-dicarboxamide, N,N'-bis[(R)-1-isopropyl-2-methyl-2-hydroxypropyl]cyclohexane-1,1-dicarboxamide, N,N'-bis[(R)-1-isopropyl-2-ethyl-2-hydroxybutyl]cyclohexane-1,1-dicarboxamide, N,N'-bis[(R)-1-isopropyl-2-n-propyl-2-hydroxypentyl]cyclohexane-1,1-dicarboxamide, N,N'-bis[(R)-1-isopropyl-2,2-diphenyl-2-hydroxyethyl]cyclohexane-1,1-dicarboxamide, N,N'-bis[(R)-1-isopropyl-2,2-di(4-methylphenyl)-2-hydroxyethyl]cyclohexane-1,1-dicarboxamide, N,N'-bis[(R)-1-isopropyl-2,2-di(2-methoxyphenyl)-2-hydroxyethyl]cyclohexane-1,1- dicarboxamide, N,N'-bis[(R)-1-isopropyl-2,2-di(4-methoxyphenyl)-2-hydroxyethyl]cyclohexane-1,1-dicarboxamide, N,N'-bis[(R)-1-isopropyl-2-benzyl-2-hydroxy-3-phenylpropyl]cyclohexane-1,1-dicarboxamide, N,N'-bis[(R)-2-methyl-1-(1-hydroxycyclobutyl)propyl]cyclohexane-1,1-dicarboxamide, N,N'-bis[(R)-2-methyl-1-(1-hydroxycyclopentyl)propyl]cyclohexane-1,1-dicarboxamide, N,N'-bis[(R)-2-methyl-1-(1-hydroxycyclohexyl)propyl]cyclohexane-1,1-dicarboxamide, N,N'-bis[R-1-isobutyl-2-hydroxyethyl]cyclohexane-1,1-dicarboxamide, N,N'-bis[(R)-1-isobutyl-2-methyl-2-hydroxypropyl]cyclohexane-1,1-dicarboxamide, N,N'-bis[(R)-1-isobutyl-2-ethyl-2-hydroxybutyl]cyclohexane-1,1-dicarboxamide, N,N'-bis[(R)-1-isobutyl-2-n-propyl-2-hydroxypentyl]cyclohexane-1,1-dicarboxamide, N,N'-bis[(R)-1-isobutyl-2,2-diphenyl-2-hydroxyethyl]cyclohexane-1,1-dicarboxamide, N,N'-bis[(R)-1-isobutyl-2,2-di(4-methylphenyl)-2-hydroxyethyl]cyclohexane-1,1-dicarboxamide, N,N'-bis[(R)-1-isobutyl-2,2-di(2-methoxyphenyl)-2-hydroxyethyl]cyclohexane-1,1-dicarboxamide, N,N'-bis[(R)-1-isobutyl-2,2-di(4-methoxyphenyl)-2-hydroxyethyl]cyclohexane-1,1-dicarboxamide, N,N'-bis[(R)-1-isobutyl-2-benzyl-2-hydroxy-3-phenylpropyl]cyclohexane-1,1-dicarboxamide, N,N'-bis[(R)-3-methyl-1-(1-hydroxycyclobutyl)butyl]cyclohexane-1,1-dicarboxamide, N,N'-bis[(R)-3-methyl-1-(1-hydroxycyclopentyl)butyl]cyclohexane-1,1-dicarboxamide, N,N'-bis[(R)-3-methyl-1-(1-hydroxycyclohexyl)butyl]cyclohexane-1,1-dicarboxamide, N,N'-bis[(R)-1-tert-butyl-2-hydroxyethyl]cyclohexane-1,1-dicarboxamide, N,N'-bis[(R)-1-tert-butyl-2-methyl-2-hydroxypropyl]cyclohexane-1,1-dicarboxamide, N,N'-bis[(R)-1-tert-butyl-2-ethyl-2-hydroxybutyl]cyclohexane-1,1-dicarboxamide, N,N'-bis[(R)-1-tert-butyl-2-n-propyl-2-hydroxypentyl]cyclohexane-1,1-dicarboxamide, N,N'-bis[(R)-1-tert-butyl-2,2-diphenyl-2-hydroxyethyl]cyclohexane-1,1-dicarboxamide, N,N'-bis[(R)-1-tert-butyl-2,2-di(4-methylphenyl)-2-hydroxyethyl]cyclohexane-1,1-dicarboxamide, N,N'-bis[(R)-1-tert-butyl-2,2-di(2-methoxyphenyl)-2-hydroxyethyl]cyclohexane-1,1-dicarboxamide, N,N'-bis[(R)-1-tert-butyl-2,2-di(4-methoxyphenyl)-2-hydroxyethyl]cyclohexane-1,1-dicarboxamide, N,N'-bis[(R)-1-tert-butyl-2-benzyl-2-hydroxy-3-phenylpropyl]cyclohexane-1,1-dicarboxamide, N,N'-bis[(R)-2,2-dimethyl-1-(1-hydroxycyclobutyl)propyl]cyclohexane-1,1-dicarboxamide, N,N'-bis[(R)-2,2-dimethyl-1-(1-hydroxycyclopentyl)propyl]cyclohexane-1,1-dicarboxamide, N,N'-bis[(R)-2,2-dimethyl-1-(1-hydroxycyclohexyl)propyl]cyclohexane-1,1-dicarboxamide, N,N'-bis[(R)-1-phenyl-2-hydroxyethyl]cyclohexane-1,1-dicarboxamide, N,N'-bis[(R)-1-phenyl-2-methyl-2-hydroxypropyl]cyclohexane-1,1-dicarboxamide, N,N'-bis[(R)-1-phenyl-2-ethyl-2-hydroxybutyllcyclohexane-1,1-dicarboxamide, N,N'-bis[(R)-1-phenyl-2-n-propyl-2-hydroxypentyl]cyclohexane-1,1-dicarboxamide, N,N'-bis[(R)-1-phenyl-2,2-diphenyl-2-hydroxyethyl]cyclohexane-1,1-dicarboxamide, N,N'-bis[(R)-1-phenyl-2,2-di(4-methylphenyl)-2-hydroxyethyl]cyclohexane-1,1-dicarboxamide, N,N'-bis[(R)-1-phenyl-2,2-di(2-methoxyphenyl)-2-hydroxyethyl]cyclohexane-1,1-dicarboxamide, N,N'-bis[(R)-1-phenyl-2,2-di(4-methoxyphenyl)-2-hydroxyethyl]cyclohexane-1,1-dicarboxamide, N,N'-bis[(R)-1-phenyl-2-benzyl-2-hydroxy-3-phenylpropyl]cyclohexane-1,1-dicarboxamide, N,N'-bis[(R)-1-phenyl-1-(1-hydroxycyclobutyl)methyl]cyclohexane-1,1-dicarboxamide, N,N'-bis[R]-1-phenyl-1-(1-hydroxycyclopentyl)methyl]cyclohexane-1,1-dicarboxamide, N,N'-bis[(R)-1-phenyl-1-(1-hydroxycyclohexyl)methyl]cyclohexane-1,1-dicarboxamide, N,N'-bis[(R)-1-benzyl-2-hydroxyethyl]cyclohexane-1,1-dicarboxamide, N,N'-bis[(R)-1-benzyl-2-methyl-2-hydroxypropyl]cyclohexane-1,1-dicarboxamide, N,N'-bis[(R)-1-benzyl-2-ethyl-2-hydroxybutyl]cyclohexane-1,1-dicarboxamide, N,N'-bis[(R)-1-benzyl-2-n-propyl-2-hydroxypentyl]cyclohexane-1,1-dicarboxamide, N,N'-bis[(R)-1-benzyl-2,2-diphenyl-2-hydroxyethyl]cyclohexane-1,1-dicarboxamide, N,N'-bis[(R)-1-benzyl-2,2-di(4-methylphenyl)-2-hydroxyethyl]cyclohexane-1,1-dicarboxamide, N,N'-bis[(R)-1-benzyl-2,2-di(2-methoxyphenyl)-2-hydroxyethyl]cyclohexane-1,1-dicarboxamide, N,N'-bis[(R)-1-benzyl-2,2-di(4-methoxyphenyl)-2-hydroxyethyl]cyclohexane-1,1-dicarboxamide, N,N'-bis[(R)-1-benzyl-2-benzyl-2-hydroxy-3-phenylpropyl]cyclohexane-1,1-dicarboxamide, N,N'-bis[(R)-2-phenyl-1-(1-hydroxycyclobutyl)ethyl]cyclohexane-1,1-dicarboxamide, N,N'-bis[(R)-2-phenyl-1-(1-hydroxycyclopentyl)ethyl]cyclohexane-1,1-dicarboxamide, N,N'-bis[(R)-2-phenyl-1-(1-hydroxycyclohexyl)ethyl]cyclohexane-1,1-dicarboxamide; and these compounds of which the configuration (R) is changed to (S).

Next, a step for obtaining the optically active cycloalkylidenebisoxazoline compound represented by the formula (4) (hereinafter, described as the optically active cycloalkylidenebisoxazoline (4)) by reacting the optically active cycloalkylidenebisamidoalcohol (3) with the sulfonylation agent in the presence of a basic compound.

Examples of the basic compound include an organic amine compound such as pyridine, 2,6-dimethylpyridine, 4-dimethylaminopyridine and triethylamine; an alkali metal hydroxide such as sodium hydroxide and potassium hydroxide; and an alkali metal alkoxide such as sodium methoxide and potassium tert-butoxide. These basic compounds may be used alone and any two or more compounds may be used at the same time. The amount of the basic compound to be used is not particularly limited and large excess thereof may be used as the solvent. The amount thereof is usually about 0.0005 to 5 moles relative to 1 mole of the optically active cycloalkylidenebisamidoalcohol (3). When two or more compounds are used at the same time, this amount is sum of number of moles thereof.

The sulfonylation agent represents at least one compound selected from the group consisting of alkylsulfonyl halides, arylsulfonyl halides, alkylsulfonyl anhydrides and arylsulfonyl anhydrides.

Examples of alkylsulfonyl halides include compounds having 1 to 5 carbon atoms having an optionally substituted alkyl group such as methanesulfonyl chloride, methanesulfonyl bromide, ethanesulfonyl chloride and ethanesulfonyl bromide. Examples of arylsulfonyl halides include C6-10 compounds having an optionally substituted aryl group such as benzenesulfonyl chloride, benzensulfonyl bromide, paratoluenesulfonyl chloride and paratoluenesulfonyl bromide. Examples of alkylsulfonyl anhydrides include C2-20 compounds having an optionally substituted alkyl group such as methanesulfonyl anhydride, ethanesulfonyl anhydride and trifluoromethanesulfonyl anhydride. Examples of arylsulfonyl anhydrides include C12-20 compounds having an optionally substituted aryl group such as benzenesulfonyl anhydride and paratoluenesulfonyl anhydride. Among these sulfonylation agents, methanesulfonyl chloride and paratoluenesulfonyl chloride are preferably used.

The amount of the sulfonylation agent to be used is usually about 1 to 5 moles relative to 1 mole of the optically active cycloalkylidenebisamidoalcohol (3).

The reaction is usually carried out in the presence of a solvent. The solvent is not particularly limited and examples thereof include aromatic hydrocarbon solvents such as toluene and xylene; halogenated hydrocarbon solvents such as chlorobenzene, dichloromethane and dichloroethane; ether solvents such as tetrahydrofuran and tert-butyl methyl ether; and a mixture thereof. The amount thereof is not particularly limited and it is usually 2 to 200 parts by weight relative to 1 part by weight of the optically active cycloalkylidenebisamidoalcohol (3).

The reaction temperature is usually a range of about −20 to 150° C., preferably a range of about 0 to 100° C.

After completion of the reaction, for example, the optically active cycloalkylidenebisoxazoline (4) can be obtained by concentrating the reaction liquid obtained. The optically active cycloalkylidenebisoxazoline (4) obtained can be purified by a conventional method such as column chromatography and recrystallization, if necessary.

The configuration of the asymmetric center represented by * in the optically active cycloalkylidenebisoxazoline (4) thus obtained is the same as that of the optically active cycloalkylidenebisamidoalcohol (3) used.

Examples of the optically active cycloalkylidenebisoxazoline (4) include 1,1-bis[2-[(4R)-methyloxazoline]]cyclopropane, 1,1-bis[2-[(4R)-methyl-5,5-dimethyloxazoline]]cyclopropane, 1,1-bis[2-[(4R)-methyl-5,5-diethyloxazoline]]cyclopropane, 1,1-bis[2-[(4R)-methyl-5,5-di-n-propyloxazoline]]cyclopropane, 1,1-bis[2-[(4R)-methyl-5,5-diphenyloxazoline]]cyclopropane, 1,1-bis[2-[(4R)-methyl-5,5-di(4-methylphenyl)oxazoline]]cyclopropane, 1,1-bis[2-[(4R)-methyl-5,5-di(2-methoxyphenyl)oxazoline]]cyclopropane, 1,1-bis[2-[(4R)-methyl-5,5-di(2-methoxyphenyl)oxazoline]]cyclopropane, 1,1-bis[2-[(4R)-methyl-5,5-di(4-methoxyphenyl)oxazoline]]cyclopropane, 1,1-bis[2-[(4R)-methyl-5,5-dibenzyloxazoline]]cyclopropane, 1,1-bis[2-[spiro[(4R)-methyloxazoline-5,1'-cyclobutane]]]cyclopropane, 1,1-bis[2-[spiro[(4R)-methyloxazoline-5,1'-cyclopentane]]]cyclopropane, 1,1-bis[2-[spiro[(4R)-methyloxazoline-5,1'-cyclohexane]]]cyclopropane, 1,1-bis[2-[(4R)-isopropyloxazoline]]cyclopropane, 1,1-bis[2-[(4R)-isopropyl-5,5-dimethyloxazoline]]cyclopropane, 1,1-bis[2-[(4R)-isopropyl-5,5-diethyloxazoline]]cyclopropane, 1,1-bis[2-[(4R)-isopropyl-5,5-di-n-propyloxazoline]]cyclopropane, 1,1-bis[2-[(4R)-isopropyl-5,5-diphenyloxazoline]]cyclopropane, 1,1-bis[2-[(4R)-isopropyl-5,5-di(4-methylphenyl)oxazoline]]cyclopropane, 1,1-bis[2-[(4R)-isopropyl-5,5-di(2-methoxyphenyl)oxazoline]]cyclopropane, 1,1-bis[2-[(4R)-isopropyl-5,5-di(2-methoxyphenyl)oxazoline]]cyclopropane, 1,1-bis[2-[(4R)-isopropyl-5,5-di(4-methoxyphenyl)oxazoline]]cyclopropane, 1,1-bis[2-[(4R)-isopropyl-5,5-dibenzyloxazoline]]cyclopropane, 1,1-bis[2-[spiro[(4R)-isopropyloxazoline-5,1'-cyclobutane]]]cyclopropane, 1,1-bis[2-[spiro[(4R)-isopropyloxazoline-5,1'-cyclopentane]]]cyclopropane, 1,1-bis[2-[spiro[(4R)-isopropyloxazoline-5,1'-cyclohexane]]]cyclopropane, 1,1-bis[2-[(4R)-tert-butyloxazoline]]cyclopropane, 1,1-bis[2-[(4R)-tert-butyl-5,5-dimethyloxazoline]]cyclopropane, 1,1-bis[2-[(4R)-tert-butyl-5,5-diethyloxazoline]]cyclopropane, 1,1-bis[2-[(4R)-tert-butyl-5,5-di-n-propyloxazoline]]cyclopropane, 1,1-bis[2-[(4R)-tert-butyl-5,5-diphenyloxazoline]]cyclopropane, 1,1-bis[2-[(4R)-tert-butyl-5,5-di(4-methylphenyl)oxazoline]]cyclopropane, 1,1-bis[2-[(4R)-tert-butyl-5,5-di(2-methoxyphenyl)oxazoline]] cyclopropane, 1,1-bis[2-[(4R)-tert-butyl-5,5-di(2-methoxyphenyl)oxazoline]]cyclopropane, 1,1-bis[2-[(4R)-tert-butyl-5,5-di(4-methoxyphenyl)oxazoline]]cyclopropane, 1,1-bis[2-[(4R)-tert-butyl-5,5-dibenzyloxazoline]] cyclopropane, 1,1-bis[2-[spiro[(4R)-tert-butyloxazoline-5,1'-cyclobutane]]]cyclopropane, 1,1-bis[2-[spiro[(4R)-tert-butyloxazoline-5,1'-cyclopentane]]]cyclopropane, 1,1-bis[2-[spiro[(4R)-tert-butyloxazoline-5,1'-cyclohexane]]] cyclopropane, 1,1-bis[2-[(4R)-phenyloxazoline]]cyclopropane, 1,1-bis[2-[(4R)-phenyl-5,5-dimethyloxazoline]]cyclopropane, 1,1-bis[2-[(4R)-phenyl-5,5-diethyloxazoline]]cyclopropane, 1,1-bis[2-[(4R)-phenyl-5,5-di-n-propyloxazoline]]cyclopropane, 1,1-bis[2-[(4R)-phenyl-5,5-diphenyloxazoline]]cyclopropane, 1,1-bis[2-[(4R)-phenyl-5,5-di(4-methylphenyl)oxazoline]]cyclopropane, 1,1-bis[2-[(4R)-phenyl-5,5-di(2-methoxyphenyl)oxazoline]]cyclopropane, 1,1-bis[2-[(4R)-phenyl-5,5-di(2-methoxyphenyl)oxazoline]]cyclopropane, 1,1-bis[2-[(4R)-phenyl-5,5-di(4-methoxyphenyl)oxazoline]]cyclopropane, 1,1-bis[2-[(4R)-phenyl-5,5-dibenzyloxazoline]]cyclopropane, 1,1-bis[2-[spiro[(4R)-phenyloxazoline-5,1'-cyclobutane]]]cyclopropane, 1,1-bis[2-[spiro[(4R)-phenyloxazoline-5,1'-cyclopentane]]]cyclopropane, 1,1-bis[2-[spiro[(4R)-phenyloxazoline-5,1'-cyclohexane]]] cyclopropane, 1,1-bis[2-[(4R)-benzyloxazoline]]cyclopropane, 1,1-bis[2-[(4R)-benzyl-5,5-dimethyloxazoline]]cyclopropane, 1,1-bis[2-[(4R)-benzyl-5,5-diethyloxazoline]]cyclopropane, 1,1-bis[2-[(4R)-benzyl-5,5-di-n-propyloxazoline]]cyclopropane, 1,1-bis[2-[(4R)-benzyl-5,5-diphenyloxazoline]]cyclopropane, 1,1-bis[2-[(4R)-benzyl-5,5-di(4-methylphenyl)oxazoline]]cyclopropane, 1,1-bis[2-[(4R)-benzyl-5,5-di(2-methoxyphenyl)oxazoline]]cyclopropane, 1,1-bis[2-[(4R)-benzyl-5,5-di(2-methoxyphenyl)oxazoline]]cyclopropane, 1,1-bis[2-[(4R)-benzyl-5,5-di(4-methoxyphenyl)oxazoline]]cyclopropane, 1,1-bis[2-[(4R)-benzyl-5,5-dibenzyloxazoline]]cyclopropane, 1,1-bis[2-[spiro[(4R)-benzyloxazoline-5,1'-cyclobutane]]]cyclopropane, 1,1-bis[2-[spiro[(4R)-benzyloxazoline-5,1'-cyclopentane]]]cyclopropane, 1,1-bis[2-[spiro[(4R)-benzyloxazoline-5,1'-cyclohexane]]] cyclopropane; and these compounds in which cross-linked ring structure at the 2-position of the oxazoline ring is replaced with a cyclobutane, cyclopentane or cyclohexane ring; and these compounds of which the configuration (4S) at the 4-positon of the oxazoline ring is changed to (4R) such as 1,1-bis[2-[(4S)-methyloxazoline]]cyclopropane.

EXAMPLES

The present invention will be further illustrated in more detail by Examples. The present invention is not limited to these Examples.

Example 1

In a 100 mL Schlenk tube purged with nitrogen, 980 mg (7.14 mmol) of (R)-phenylglycinol, 565 mg (3.57 mmol) of dimethyl 1,1-cyclopropanedicarboxylate, 6.8 mg (0.18 mmol) of lithium methoxide and 40 mL of normal heptane were mixed and the resulting mixture was stirred at 100° C. for 3 hours. The homogeneous solution changed to a white suspension as the reaction progresses. After that, reaction solution was cooled to room temperature and filtered. The obtained powder was dried to obtain 1.19 g of a white powder of N,N'-bis[(R)-1-phenyl-1-(1-hydroxycyclohexyl)methyl] cyclopropane-1,1-dicarboxamide.

Yield: 90% (based on dimethyl 1,1-cyclopropanedicarboxylate).

$^1$H-NMR (δ: ppm, $CD_3S(O)CD_3$ solvent, TMS standard) 8.64 (d, J=8.60 Hz, 2H), 7.32-7.19 (m, 10H), 5.01 (s, 2H), 4.90 (q, 6.73 Hz, 2H), 3.59 (d, 5.2 Hz, 4H), 1.30 (s, 4H)

Example 2

According to the same manner as that described in Example 1, 1.28 g of a white powder of N,N'-bis[(S)-1-tert-butyl-2-hydroxyethyl]cyclopropane-1,1-dicarboxamide was obtained except that 980 mg (8.36 mmol) of (S)-tert-leucinol, 655 mg (4.14 mmol) of dimethyl 1,1-cyclopropanedicarboxylate and 7.9 mg (0.21 mmol) of lithium methoxide were used as each reaction agent.

Yield: 94% (based on dimethyl 1,1-cyclopropanedicarboxylate).

$^1$H-NMR (δ: ppm, $CD_3S(O)CD_3$ solvent, TMS standard) 7.76 (d, J=9.56 Hz, 2H), 4.58 (t, J=5.20 Hz, 2H), 3.72 (dt, J=9.34 Hz, J=3.50 Hz, 2H), 3.63-3.57 (m, 2H), 3.41-3.34 (m, 2H), 1.29-1.23 (m, 2H), 1.10-1.05 (m, 2H), 0.82 (s, 18H)

Example 3

According to the same manner as that described in Example 2, 640 mg of a white powder of N,N'-bis[(S)-1-tert-butyl-2-hydroxyethyl]cyclopropane-1,1-dicarboxamide was obtained except that 507 mg (4.32 mmol) of (S)-tert-leucinol, 342 mg (2.16 mmol) of dimethyl 1,1-cyclopropanedicarboxylate and 4.5 mg (0.11 mmol) of lithium hydroxide monohydrate were used as each reaction agent.

Yield: 90% (based on dimethyl 1,1-cyclopropanedicarboxylate).

Example 4

According to the same manner as that described in Example 2, 1.38 g of a white powder of N,N'-bis[(S)-1-tert-butyl-2-hydroxyethyl]cyclohexane-1,1-dicarboxamide was obtained except that 945 mg (4.14 mmol) of diethyl 1,1-cyclohexanedicarboxylate was used in place of dimethyl 1,1-cyclopropanedicarboxylate used in Example 2.

Yield: 90% (based on dimethyl 1,1-cyclohexanedicarboxylate).

$^1$H-NMR (δ: ppm, $CD_3S(O)CD_3$ solvent, TMS standard) 6.96 (d, J=9.49 Hz, 2H), 4.48 (t, J=5.68 Hz, 2H), 3.77-3.70 (m, 2H), 3.59-3.52 (m, 2H), 3.44-3.35 (m, 2H), 1.98-1.95 (m, 4H), 1.45-1.37 (m, 6H), 0.83 (s, 18H)

Comparative Example 1

According to the same manner as that described in Example 3, the reaction did not proceed and (S)-tert-leucinol and dimethyl cyclopropanedicarboxylate, which are starting materials, were recovered except that lithium methoxide was not used in Example 3.

Example 5

In a 100 mL Schlenk tube purged with nitrogen, 490 mg (1.49 mmol) of N,N'-bis[(S)-1-tert-butyl-2-hydroxyethyl]cyclopropane-1,1-dicarboxamide, 664 mg (6.56 mmol) of triethylamine, 18.2 mg (0.15 mmol) of 4-dimethylaminopyridine and 30 mL of dichloromethane were mixed and a homogeneous solution was obtained. The solution was cooled to 0° C. After 345 mg (3.01 mmol) of methanesulfonyl chloride was added dropwise to the solution over 10 minutes at the same temperature, the resulting mixture was heated to 20° C. and stirred for 12 hours. After a saturated aqueous ammonium chloride solution was added thereto and stirred for 10 minutes at room temperature, the separation was conducted to obtain the oil layer. After the oil layer was washed with 20 mL of a saturated aqueous sodium hydrogen carbonate solution, a separation was conducted. The oil layer was dried over 5 g of anhydrous sodium sulfate. This reaction liquid was filtered and the obtained filtrate was concentrated. The residue was purified by column chromatography (alumina neutral, hexane:ethyl acetate=10:1 (v/v)) to yield 339 mg of a white powder of 1,1-bis[2-[(4S)-tert-butyloxazoline]]cyclopropane.

Yield: 77%.

$^1$H-NMR (δ: ppm, $CD_3Cl_3$ solvent, TMS standard) 4.22-4.10 (m, 4H), 3.85-3.79 (m, 2H), 1.52-1.48 (m, 2H), 1.29-1.24 (m, 2H), 0.86 (s, 18H)

Example 6

According to the same manner as that described in Example 5, 458 mg of a white powder of 1,1-bis[2-[(4S)-tert-butyloxazoline]]cyclohexane was obtained except that 552 mg (1.49 mmol) of N,N'-bis[(S)-1-tert-butyl-2-hydroxyethyl]cyclohexane-1,1-dicarboxamide was used in place of 490 mg (1.49 mmol) of N,N'-bis[(S)-1-tert-butyl-2-hydroxyethyl]cyclopropane-1,1-dicarboxamide used in Example 5.

Yield: 92%.

$^1$H-NMR (δ: ppm, $CD_3Cl_3$ solvent, TMS standard) 4.16-4.02 (m, 4H), 3.90-3.84 (m, 2H), 2.15-2.07 (m, 2H), 1.98-1.91 (m, 2H), 1.69-1.66 (m, 2H), 1.55-1.42 (m, 4H), 0.89 (s, 18H)

Example 7-1

Synthesis of (S)-t-leucinol

To a 100 mL Schlenk tube purged with nitrogen, 2.00 g (15.3 mmol) of (S)-tert-leucine and 10 mL of tetrahydrofuran were added and the inner temperature was adjusted to 10° C. To this suspension, 30.5 mL (30.5 mmol) of 1M borane-tetrahydrofuran solution was added dropwise over 30 minutes and the resulting mixture was heated to an inner temperature of 65° C. and stirred at the same temperature for 5 hours. After the reaction mixture was cooled to 10° C., 4 mL of methanol was added dropwise thereto over 10 minutes. After reaction mixture was concentrated using an evaporator, 20 mL of 4M aqueous sodium hydroxide solution was added thereto and stirred at room temperature for 1 hour. Next, the extraction was conducted by adding 30 mL of chloroform and the organic layer obtained was dehydrated over sodium sulfate. Sodium sulfate was removed by filtration and chloroform was distilled away by atmospheric distillation. Further, 1.43 g of (S)-tert-leucinol was obtained as a fraction of 70 to 75° C. by reduced-pressure distillation (0.3 kPa).

Yield: 80%.

Example 7-2

Synthesis of N,N'-bis[(S)-1-tert-butyl-2-hydroxyethyl]cyclopropane-1,1-dicarboxamide According to the same manner as that described in Example 2, 1.28 g of a white powder of N,N'-bis[(S)-1-tert-butyl-2-hydroxyethyl]cyclopropane-1,1-dicarboxamide was obtained except that 980 mg (8.36 mmol) of (S)-tert-leucinol obtained in Example 7-1 was used.

Yield: 93% (based on dimethyl 1,1-cyclopropanedicarboxylate).

Example 7-3

Synthesis of 1,1-bis[2-[(4S)-1-tert-butyloxazoline]]cyclopropane

According to the same manner as that described in Example 5, 344 mg of a white powder of 1,1-bis[2-[(4S)-tert-butyloxazoline]]cyclopropane was obtained except that 490 mg (1.49 mmol) of N,N'-bis[(S)-1-tert-butyl-2-hydroxyethyl]cyclopropane-1,1-dicarboxamide obtained in Example 7-2 was used.

Yield: 79%.

Example 8-1

Synthesis of (S)-t-leucinol

To a 100 mL Schlenk tube purged with nitrogen, 4.00 g (30.5 mmol) of (S)-tert-leucine and 40 mL of tetrahydrofuran were added and the inner temperature was adjusted to 10° C. To this suspension, 1.46 g (61.0 mmol) of lithium borohydride was added over 5 minutes and the inner temperature thereof was adjusted to 20° C. 7.44 g (67.1 mmol) of trimethylsilyl chloride was added dropwise thereto over 30 minutes and the mixture was heated to the inner temperature of 65° C. and stirred at the same temperature for 3 hours. After the reaction mixture was cooled to 10° C., 4 mL of methanol was added dropwise thereto over 20 minutes. After reaction mixture was concentrated using an evaporator, 40 mL of 4M aqueous sodium hydroxide solution was added thereto and stirred at room temperature for 1 hour. Next, the extraction was conducted by adding 40 mL of tert-butyl methyl ether and the organic layer obtained was dehydrated over sodium sulfate. Sodium sulfate was removed by filtration and tert-butyl methyl ether was distilled away by atmospheric distillation. Further, 2.96 g of (S)-tert-leucinol was obtained as a fraction of 70 to 75° C. by reduced-pressure distillation (0.3 kPa).

Yield: 83%.

Example 8-2

Synthesis of N,N'-bis[(S)-1-tert-butyl-2-hydroxyethyl]cyclopropane-1,1-dicarboxamide According to the same manner as that described in Example 2, 3.39 g of a white powder of N,N'-bis[(S)-1-tert-butyl-2-hydroxyethyl]cyclopropane-1,1-dicarboxamide was obtained except that 2.55 g (21.8 mmol) of (S)-tert-leucinol obtained in Example 8-1, 1.72 g (10.9 mmol) of dimethyl 1,1-cyclopropanedicarboxylate and 20.7 mg (0.54 mmol) of lithium methoxide were used.

Yield: 95% (based on dimethyl 1,1-cyclopropanedicarboxylate).

Example 8-3

Synthesis of 1,1-bis[2-[(4S)-tert-butyloxazoline]]cyclopropane 2.70 g (8.22 mmol) of N,N'-bis[(S)-1-tert-butyl-2-hydroxyethyl]cyclopropane-1,1-dicarboxamide obtained in Example 8-2, 3.66 g (36.2 mmol) of triethylamine, 100 mg (0.82 mmol) of 4-dimethylaminopyridine and 30 mL of tetrahydrofuran were added and a homogeneous solution was obtained. The solution was cooled to 10° C. After 2.07 g (18.1 mmol) of methanesulfonyl chloride was added dropwise thereto over 10 minutes at the same temperature, the resulting mixture was heated to 60° C. and stirred for 2 hours. After a saturated aqueous ammonium chloride solution was added thereto and stirred for 10 minutes at room temperature, the separation was conducted to obtain the oil layer. After the oil layer was washed with 20 mL of a saturated aqueous sodium hydrogen carbonate solution, a separation was conducted to obtain the oil layer. The oil layer was dried over 5 g of anhydrous sodium sulfate. This reaction liquid was filtered and the obtained filtrate was concentrated. The residue was purified by column chromatography (alumina neutral, hexane:ethyl acetate=10:1 (v/v)) to yield 1.85 g of a white powder of 1,1-bis[2-[(4S)-tert-butyloxazoline]]cyclopropane.

Yield: 77%.

Reference Example

In a 50 mL Schlenk tube purged with nitrogen, 6.47 mg (0.025 mmol) of copper(I) trifluoromethanesulfonate toluene complex, 8.00 mg of 1,1-bis[2-[(4S)-tert-butyloxazoline]]cyclopropane and 5 mL of dichloroethane were added and the resulting mixture was stirred at room temperature for 10 minutes to obtain a solution containing an asymmetric copper complex. Then, 8.81 g (50 mmol) of isobutenylmethyl benzyl ether was added thereto and the inner temperature was adjusted to 0° C. 10 mL of dichloroethane solution containing 2.85 g (25 mmol) of ethyl diazoacetate was added dropwise thereto over 2 hours and the resulting mixture was stirred at the same temperature for 30 minutes to effect reaction and the solution containing ethyl 3,3-dimethyl-2-(benzyloxymethyl)cyclopropanecarboxylate was obtained.

Yield: 82% (based on ethyl diazoacetate).

Trans-isomer/cis-isomer ratio: 94/6.

(Herein, the trans-isomer means the compound having the ester group at 1-position and benzyloxymethyl group at 2-position on the opposite side with respect to the cyclopropane ring plane and the cis-isomer means the compound having the ester group at 1-position and benzyloxymethyl group at 2-position on the same side.)

The reaction mixture was concentrated and a 1 g of the oily matter obtained was taken out. 4 mL of 2N aqueous sodium hydroxide was added thereto and the resulting mixture was stirred at an inner temperature of 100° C. for 2 hours. The neutralization by 1N hydrochloric acid, the extraction by hexane and the concentration were conducted to obtain 3,3-dimethyl-2-benzyloxymethylcyclopropanecarboxylic acid.

Optical purity: trans-isomer 97% e.e. (+-isomer), cis-isomer 11% e.e. (+-isomer)

INDUSTRIAL APPLICABILITY

According to the present invention, an optically active cycloalkylidenebisoxazoline compound, which is an important compound as a ligand of an asymmetric synthesis catalyst, can be efficiently produced.

The invention claimed is:

1. A method for producing the optically active cycloalkylidenebisamidoalcohol compound represented by the formula (3):

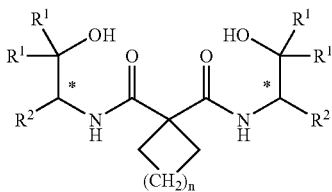

wherein R¹ represents a C1-6 alkyl group, an optionally substituted phenyl group, an optionally substituted aralkyl group or a hydrogen atom, or two R¹s, which are bonded to the same carbon atom, are bonded to form a ring together with the carbon atom to which they are bonded, R² represents a C1-6 alkyl group, an optionally substituted phenyl group or an optionally substituted aralkyl group, n represents an integer of 0 to 3, and * represents an asymmetric center, which comprises reacting an optically active aminoalcohol compound represented by the formula (1):

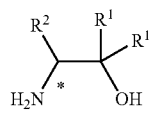

wherein R¹, R² and * are as defined above, with a cycloalkylidenemalonic acid diester compound represented by the formula (2):

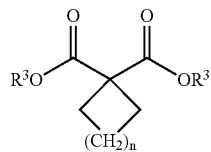

wherein R³ represents a C1-3 alkyl group and n represents an integer of 0 to 3, in the presence of a lithium compound.

2. The method according to claim 1, which further comprises a step for obtaining an optically active cycloalkylidenebisoxazoline compound represented by the formula (4):

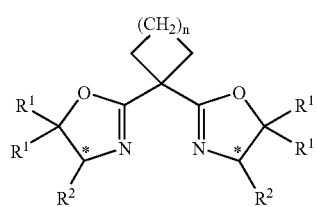

wherein R¹ represents a C1-6 alkyl group, an optionally substituted phenyl group, an optionally substituted aralkyl group or a hydrogen atom, or two R¹s, which are bonded to the same carbon atom, are bonded to form a ring together with the carbon atom to which they are bonded, R² represents a C1-6 alkyl group, an optionally substituted aralkyl group or an optionally substituted phenyl group, n represents an integer of 0 to 3, and * represents an asymmetric center, by reacting the optically active cycloalkylidenebisamidoalcohol compound represented by the formula (3) with a sulfonylation agent in the presence of a basic compound.

3. The method according to claim 1, wherein the lithium compound is at least one lithium compound selected from lithium hydroxide, a lithium alkoxide and a lithium halide.

4. The method according to claim 3, wherein the lithium alkoxide is lithium methoxide or lithium ethoxide.

5. The method according to claim 3, wherein the lithium halide is lithium chloride.

6. The method according to claim 1 or 2, wherein the reaction is carried out while removing an alcohol produced as a by-product represented by the formula (4):

R³OH (5)

wherein R³ represents a C1-3 alkyl group.

7. The method according to claim 1, wherein the optically active aminoalcohol compound represented by the formula (1) is the optically active aminoalcohol compound obtained by reacting an optically active amino acid or the ester thereof represented by the formula (6):

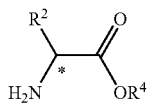

wherein R² represents a C1-6 alkyl group, an optionally substituted aralkyl group or an optionally substituted phenyl group, R⁴ represents a C1-4 alkyl group or a hydrogen atom and * represents an asymmetric center, with a borohydride compound.

8. The method according to claim 2, wherein the sulfonylation agent is paratoluenesulfonyl chloride or methanesulfonyl chloride.

9. The method according to claim 1 or 2, wherein R¹ represents a C1-6 alkyl group; a phenyl group which may be substituted with at least one selected from a C1-6 alkyl group and a C1-6 alkoxy group; a C7-16 aralkyl group which may be substituted with at least one substituent selected from a C1-6 alkyl group and a C1-6 alkoxy group; or a hydrogen atom; or two R¹s, which are bonded to the same carbon atom, are bonded to form a C3-6 cycloalkane together with the carbon atom to which they are bonded, and R² represents a C1-6 alkyl group; a phenyl group which may be substituted with at least one selected from a C1-6 alkyl group and a C1-6 alkoxy group; or a C7-16 aralkyl group which may be substituted with at least one substituent selected from a C1-6 alkyl group and a C1-6 alkoxy group.

10. The method according to claim 9, wherein R² represents a phenyl, 3-methylphenyl, 4-methylphenyl, 2-methoxyphenyl or 4-methoxyphenyl group.

* * * * *